United States Patent
Nassof et al.

(10) Patent No.: US 6,704,681 B1
(45) Date of Patent: Mar. 9, 2004

(54) METHOD AND APPARATUS FOR SENSING MICROBIAL GROWTH CONDITIONS

(75) Inventors: Russell S. Nassof, Scottsdale, AZ (US); Ryan Kuhn, Surprise, AZ (US); Michael Lee, Gilbert, AZ (US)

(73) Assignee: Envirnomics Southwest, LLC, Phoenix, AZ (US)

(*) Notice: Subject to any disclaimer, the term of this patent is extended or adjusted under 35 U.S.C. 154(b) by 0 days.

(21) Appl. No.: 10/330,564

(22) Filed: Dec. 27, 2002

(51) Int. Cl.[7] .................................................. F25D 17/06
(52) U.S. Cl. ............................................. 702/132; 165/1
(58) Field of Search ............................... 702/132, 136, 702/34; 165/1, 16; 204/230.2, 230.6, 515

(56) References Cited

U.S. PATENT DOCUMENTS 5,179,998 A * 1/1993 Des Champs ................ 165/222
6,117,295 A * 9/2000 Bjerke et al. ................ 204/515

OTHER PUBLICATIONS

Hiroyuji Fujita; "Environmental Sensor", IEEE 1994 pges 1513–1514.*
Prediction of Toxigenic Fungal Growth in Buildings by Using a Novel Modelling System. Applied and Environmental Microbiology, Nov. 1999, p. 4814–4821 vol. 65, No. 11.
Effects of Temperature and Relative Humidity on Spore Germination of Mycotoxic Species of Aspergillus and Penicillium. Mycologia, vol. 67, 175 p. 1187–1189.
Moisture Movement in Walls in a Warm Climate. by A. Tenwolde and H.T. Mel, PH.D.

* cited by examiner

Primary Examiner—Kamini Shah
(74) Attorney, Agent, or Firm—Jordan M. Meschkow; Lowell W. Gresham; Meschkow & Gresham, PLC

(57) ABSTRACT

This method and device collect relative humidity data, then evaluate that data using an algorithm to determine if conditions are permissible for fungal growth. The growth condition meter, placed in a building's wall or ceiling, includes a simple controller attached to a memory, a timer, a relative humidity sensor, and a user interface. The device executes an algorithm for determining growth conditions based on a 24-hour history of relative humidity samples. First, the algorithm determines if relative humidity levels follow a cyclical profile similar to typical environmental conditions. In addition, it verifies that enough time is spent below a temporal humidity threshold. Second, the algorithm performs a baseline analysis comparing all samples over the previous 24-hour period to determine if all samples are over a fixed threshold. This allows for a situation where enough time is spent below the temporal threshold but overall relative humidity remains too high.

20 Claims, 5 Drawing Sheets

METHOD AND APPARATUS FOR SENSING MICROBIAL GROWTH CONDITIONS

BACKGROUND OF THE INVENTION

Field of the Invention: The present invention relates generally to systems for monitoring environmental conditions and, more particularly, to detection of environmental conditions in buildings that are conducive to fungal growth.

State of the Art: There is a growing concern about fungal contamination in both residential and commercial buildings. To address this concern, there is a need for a system that detects environmental conditions conducive to growth of some of the most common fungal types found in contaminated buildings.

Fungal contamination in buildings and the subsequent exposure risk to inhabitants is an increasing concern to builders, property managers and owners, and the property insurance companies that issue coverage. Although the low cost of laboratory analysis has made accurately assessing fungal contamination in residences and buildings possible, the associated costs of remediating fungal-contaminated buildings remains high, due to specialized practices and procedures not found in conventional demolition and construction. In light of this, we sought a method by which the conditions for permissible fungal growth could be detected and corrected before fungal contamination occurs.

Generally, fungi require nutritious media, moisture, and mild temperatures to grow. Although nutritious media and mild temperatures are often found in living and working spaces, relative humidity and surface moisture are often too low for fungal growth to occur. In walls, roof/ceilings, and other plenum spaces however, these contained areas create an environment favorable for mold growth and thus these spaces represent the highest risk for mold development. Indeed, plumbing, appliance, and roof leaks in plenum areas are often causes of loss leading to fungal contamination in a building. The moisture requirement for fungal growth is fulfilled by accidental water incursions, and can be artificially divided into fast, catastrophic leaks and slower leaks. Although catastrophic leaks typically result in the greatest water-related damage, their very nature results in relatively rapid detection and subsequent prevention or remediation of fungal contamination, if handled expeditiously. Slow water incursions such as those related to HVAC system issues, leaking appliances, groundwater incursions, plumbing leaks, and roof leaks are of particular concern, since inhabitants do not always readily detect them.

A small unobtrusive and inexpensive device is needed for detecting these relative humidity levels conducive to fungal growth. In addition, a method and device are needed for analyzing the relative humidity values. Results of the analysis may be reported to a user through a visual and auditory interface or to a host device through a network interface.

BRIEF SUMMARY OF THE INVENTION

In one preferred embodiment of the present invention, a device and method collect and log relative humidity, and evaluate that data using an algorithm to determine if local environmental conditions are conducive for fungal growth of potentially toxicogenic species of Aspergillus, Penicillium, and Stachybotrys, molds commonly found in the United States. The device and method detect conditions conducive to the growth of several species of fungus (mold) and not necessarily mold itself.

In one embodiment, the device, a fungus growth condition meter, is placed in a wall, floor, or ceiling to detect relative humidity levels within the wall or attic cavities. It is particularly useful for placing in "wet" walls where plumbing exists and the danger of pipe leakage makes a fungal growth condition more probable. The device may be configured in a cylindrical shape, similar to a hockey puck, or as a rectangular cube suitable for placing in a standard electrical box such as those used to house AC electrical current outlets. A panel on the front of the device indicates growth conditions within the cavity to a user. The interface may comprise a visual alarm, such as a blinking light emitting diode LED, an audio alarm, and a display indicating up to five different levels of relative humidity conditions.

The growth condition meter may include a simple controller with attached memory, a timer, a relative humidity sensor, and the user interface. The timer keeps track of the time of day and creates a fixed time interval at which relative humidity values are sampled using the relative humidity sensor. In addition, the growth condition meter may contain a network interface for connection to a host computer allowing the creation of a network of growth condition meters positioned throughout a building. The host computer may be a standard personal computer, a computer specifically designed for the task of monitoring growth condition meters, or possibly even a personal digital assistant (PDA) or similar device.

In one preferred embodiment, the device executes an algorithm for determining growth conditions within the cavity based on a history of relative humidity samples. To begin the process, the growth condition meter gathers enough samples at a predetermined sampling interval to complete a 24-hour period of aggregate samples. The algorithm then compares the relative humidity samples to predetermined relative humidity thresholds to determine a severity level for fungal growth. The algorithm uses a two-part analysis rubric.

First, the algorithm uses a temporal analysis rubric. This analysis examines all consecutive samples over the previous 24-hour period to determine how long the relative humidity was below a predetermined threshold. Relative humidity levels will typically by cyclical, following a roughly sinusoidal profile over a 24-hour period. By examining consecutive relative humidity values below a fixed threshold, the algorithm can verify that relative humidity is varying in relation to environmental conditions. Additionally, the algorithm verifies that enough time is spent below the threshold creating a thermal burn-off of the humidity to an extent that mold growth is not probable. The threshold level is set to a predetermined programmable value based on environmental conditions where the growth condition meter is installed. Example historical data collected in Houston, Texas indicate that, for the Houston area, a relative humidity threshold of about 80% would be appropriate.

The second rubric is a baseline analysis comparing all samples over the previous 24-hour period to determine if all samples are over a predetermined relative humidity threshold. The baseline rubric allows for a scenario where there is enough time spent below the temporal threshold but the overall relative humidity remains high enough to permit fungal growth. Comparing the relative humidity values to three different threshold levels creates a gradient severity level based on this baseline analysis. The threshold levels are set to predetermined programmable values based on environmental conditions where the growth condition meter is installed. Example historical data collected in the Houston, Texas area indicate that, for the Houston area, appropriate threshold levels are 75%, 70%, and 65%.

The algorithm combines the results of both analysis rubrics to arrive at a composite severity level, which it then reports to the user through the user interface or to a host computer through the network.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE INVENTION

A minimum relative humidity value required for fungus growth can be identified for the following fungal types:

*Aspergillus flavus*

*Aspergillus nidulans*

*Aspergillus ochraceus*

*Aspergillus versicolor*

*Penicillium citrinum*

*Penicillium cyclopium*

*Penicillium urticae*

*Penicillium viridicaturn*

*Stachybotrys chartarum*

The permissible relative humidity varies for different fugal type organisms. However, for the Aspergillus and Penicillium type listed above, fungus growth often begins when relative humidity is about 80% or more. Relative humidity values conducive to growth may in fact be higher for several fungal types in the list. However, by targeting fungal types with lower relative humidity requirements, growth prediction for fungal types with higher requirements is achieved.

Due to high relative humidity and mild temperatures year-round, the city of Houston and its surrounding areas was chosen as a model metropolitan area to compare permissible relative humidity values and actual ambient relative humidity. Relative humidity in Houston follows a cyclic pattern over a 24-hour period. Peaks and troughs shift based on the season, as do the high and low humidity levels. Regardless of the month or season, relative humidity is typically likely to be greater than or equal to about 80% for a little less than half of a typical 24-hour day, leaving a little more than half the day where relative humidity is below about 80%. By comparing the number of local, hourly readings that are above or equal to 80% relative humidity to historic values, it is possible to discriminate between natural and artificial (e.g. water incursions) relative humidity levels.

Houston is an exemplary area. Changes in the threshold value conducive to mold growth, the amount of time above the threshold, the amount of time below the threshold, and the cyclical nature of the variations will vary for different environmental and weather conditions. These variations are accounted for within the scope of the present invention.

Figure 1A:
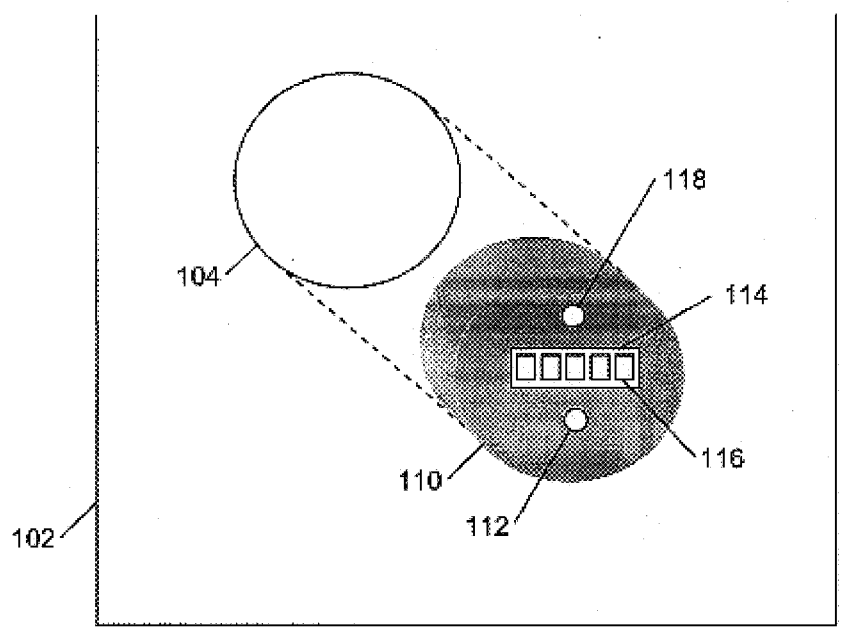
FIGS. 1A and 1B are perspective views of two exemplary physical configurations for the microbial growth condition meter.
Figure 1B:
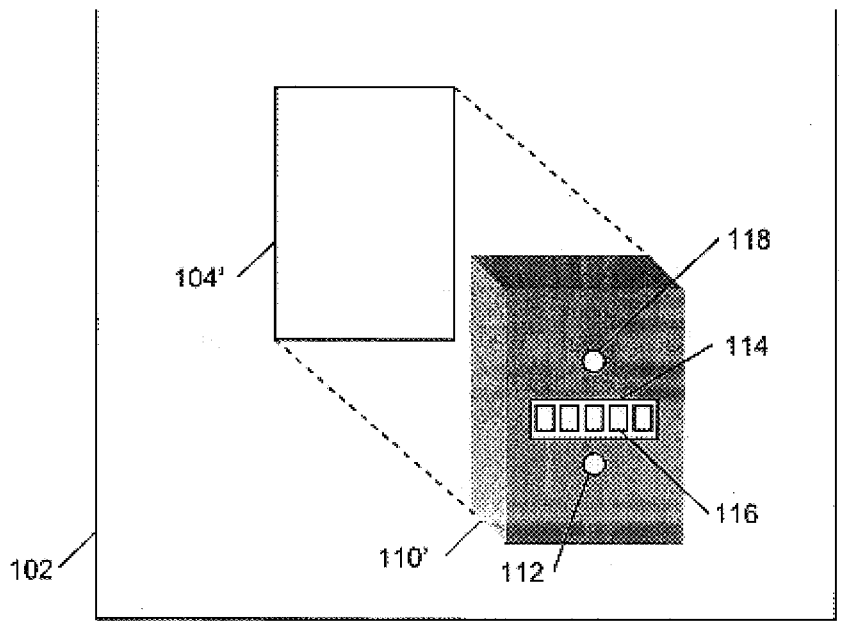

Referring first to FIGS. 1A and 1B, exemplary physical configurations of a growth condition meter 110 are shown.

FIG. 1A depicts the growth condition meter 110 as a cylindrical shape similar to a hockey puck. The growth condition meter 110 is inserted into a circular cavity 104 of a wall 102 within a building. Upon the face of the growth condition meter 110 are a user notification panel 114, an alarm light emitting diode (LED) 118, and a klaxon-type horn as an audible alarm 112. The user notification panel 114, in the currently preferred embodiment, contains five LEDs 116 in a color gradient from green to red. The number of LED elements illuminated indicates five levels of growth condition severity. No LEDs 116 illuminated indicates little microbial growth danger. All five LEDs 116 illuminated indicate a severe microbial growth danger. Additionally, in a condition where all five LEDs 116 of the user notification panel 114 are illuminated, the alarm LED 118 will blink at a high rate, and the audible alarm 112 will sound.

FIG. 1B shows an alternate physical configuration for the growth condition meter 110. In this physical configuration, the growth condition meter 110 is in a rectangular box shape. The growth condition meter 110' is inserted into a rectangular cavity 104' in the wall 102 within a building. The rectangular cavity 104' is a size consistent for use with standard electrical boxes used for installing AC electricity receptacles, telephone connectors, and television antenna connectors.

The user notification panel 114 may be substituted or augmented with a liquid crystal display, or other type of visual feedback, with numbers or symbols correlated to the five level severity index. Clearly, the placement of the notification panel 114, alarm LED 118, and audible alarm 112, may be in any configuration and located anywhere convenient for the user. In addition, the cylinder and rectangular box configurations are two examples of currently preferred embodiments, many other shapes and sizes are possible and fully within the scope of the presently claimed invention.

When placed in a wall, for beneficial results the growth condition meter 110 may be placed on the lower portion the wall. However, for measuring attic or inter-level relative humidity conditions, the growth condition meter 110 may also be placed in a ceiling or floor.

Figure 2:
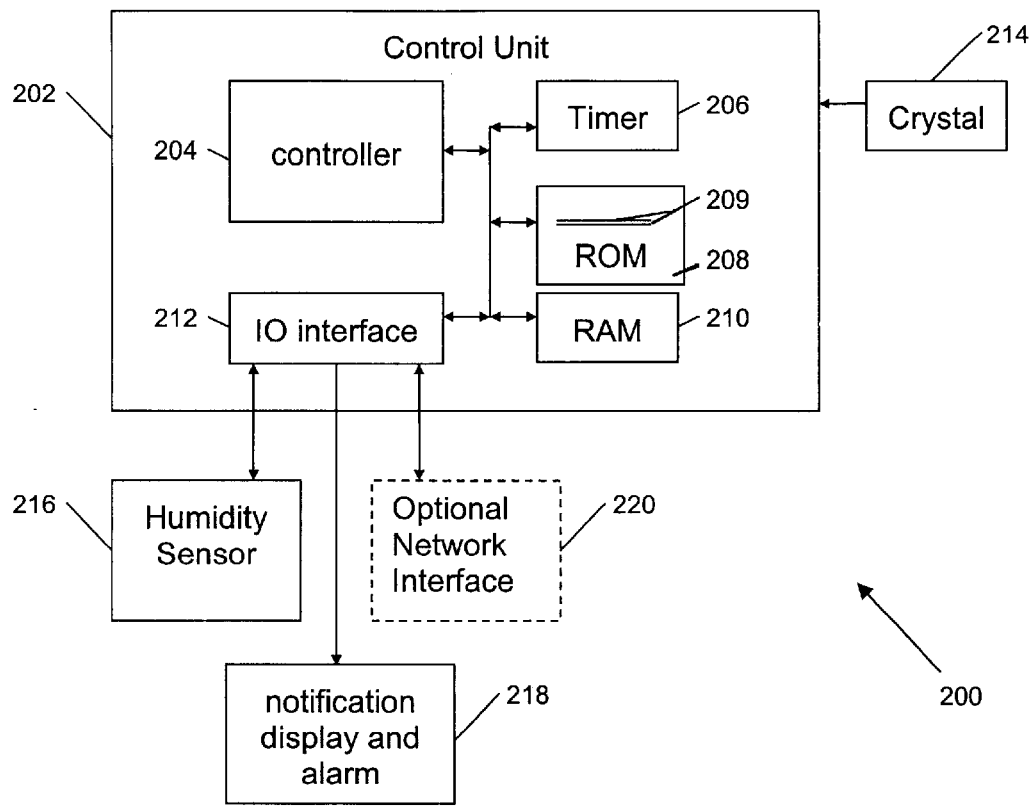
FIG. 2 is a block diagram of the growth condition meter.

FIG. 2 shows a functional block diagram of a preferred embodiment of the growth condition meter 200. A control unit 202 manages overall operation. The control unit 202 is comprised of a controller 204, a timer 206, a read only memory (ROM) 208, a random access memory (RAM) 210, and an input/output (IO) interface 212. Connected to the control unit 202 are a crystal 214, a relative humidity sensor 216, a notification display and alarm interface 218, and an optional network interface 220.

A simple 8-bit micro-controller, such as the MicroChip® PIC16C72, is appropriate to fulfill all the functions within the control unit 202.

The ROM 208 stores a program of executable instructions 209 that implement sampling and notification algorithms as described below. All program execution is performed by the controller 204. Enough RAM 210 is needed to store any required temporary variables of the program and a 24-hour history table of relative humidity samples.

The crystal 214 provides an operating frequency for the microcontroller 204. Additionally, the timer 206 uses the crystal 214 frequency to create a sampling interval interrupt to the controller 204.

A relative humidity sensor 216 connects to the control unit 202 through the IO interface 212. The relative humidity sensor should be able to detect a full range from at least one to 99 percent relative humidity. Most relative humidity sensors, such as the Humirel HS1100, are based on a capacitive cell and change capacitance values at different relative humidity levels. Therefore, the interface between the relative humidity sensor 216 and the control unit 202 may take on many forms. The relative humidity sensor 216 could be connected directly to an analog to digital converter (not shown). At the sampling time, the control unit 202 could then charge the relative humidity sensor 216 to a high voltage level. The control unit 202 then removes the voltage and times a decay rate, determining the capacitance value, and therefore the relative humidity level, based on the decay rate. The relative humidity sensor 216 could also be connected through a simple operational amplifier oscillator circuit (not shown) having a frequency that varies in proportion to the capacitance. The control unit 202 could then sample the frequency rate to indirectly determine the relative humidity value.

The notification display 116, alarm LED 118, and audible alarm 112 are connected to the control unit 202 through the notification display and alarm interface 218.

In addition, an optional network interface 220 may be connected to the control unit 202, through the IO interface 212. The network interface may be any of many popular digital network connections, such as RS-232, Universal Serial Bus (USB), Ethernet, IEEE 1394 (firewire), or a wireless network such Bluetooth and IEEE 802.1 a/b/g. A minimal amount of data needs to be transmitted with plenty of time in which it may be transferred. As a result, the network does not need to be fast, however, if a wired network is used the cable lengths may be long so a network connection with high noise immunity would be desirable.

Figure 3:
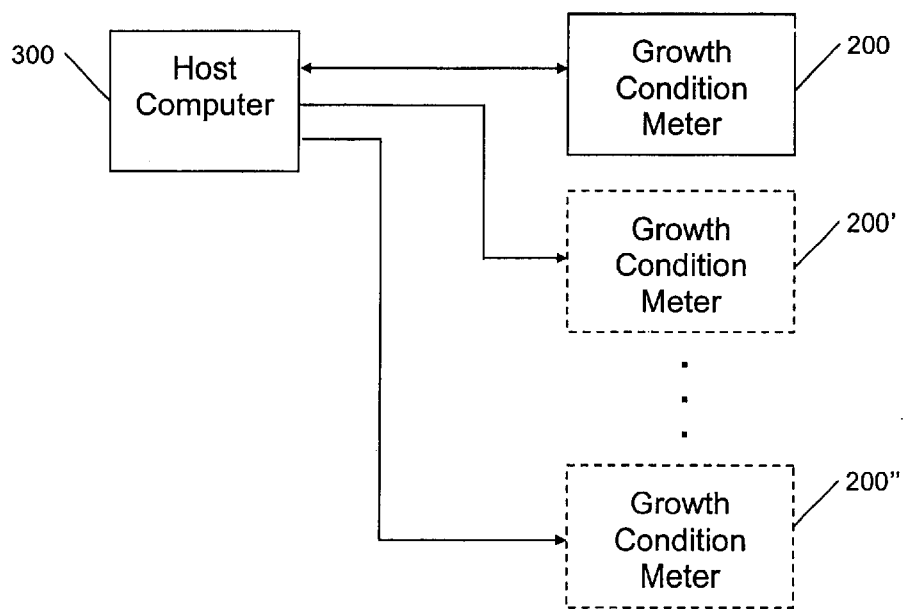
FIG. 3 is a block diagram of a computing system including multiple growth condition meters.

FIG. 3 shows a network of growth condition meters 200. In this configuration, a host computer 300 connects to one or more growth condition meters 200, 200', and 200". In this configuration, the host computer 300 can collect more detailed severity level information and store historical data for later analysis and display. In addition, the host computer can download data to the individual growth condition meters 200 to modify threshold levels, and update controller code. This host computer 300 could track all growth condition meter 200 results for analysis and possible detailed user displays indicating relative humidity levels and fungus growth potential throughout a building. This host computer 300 may be a standard personal computer, a computer specifically designed for the task of monitoring growth condition meters 200, a PDA, or similar device.

Figure 4:
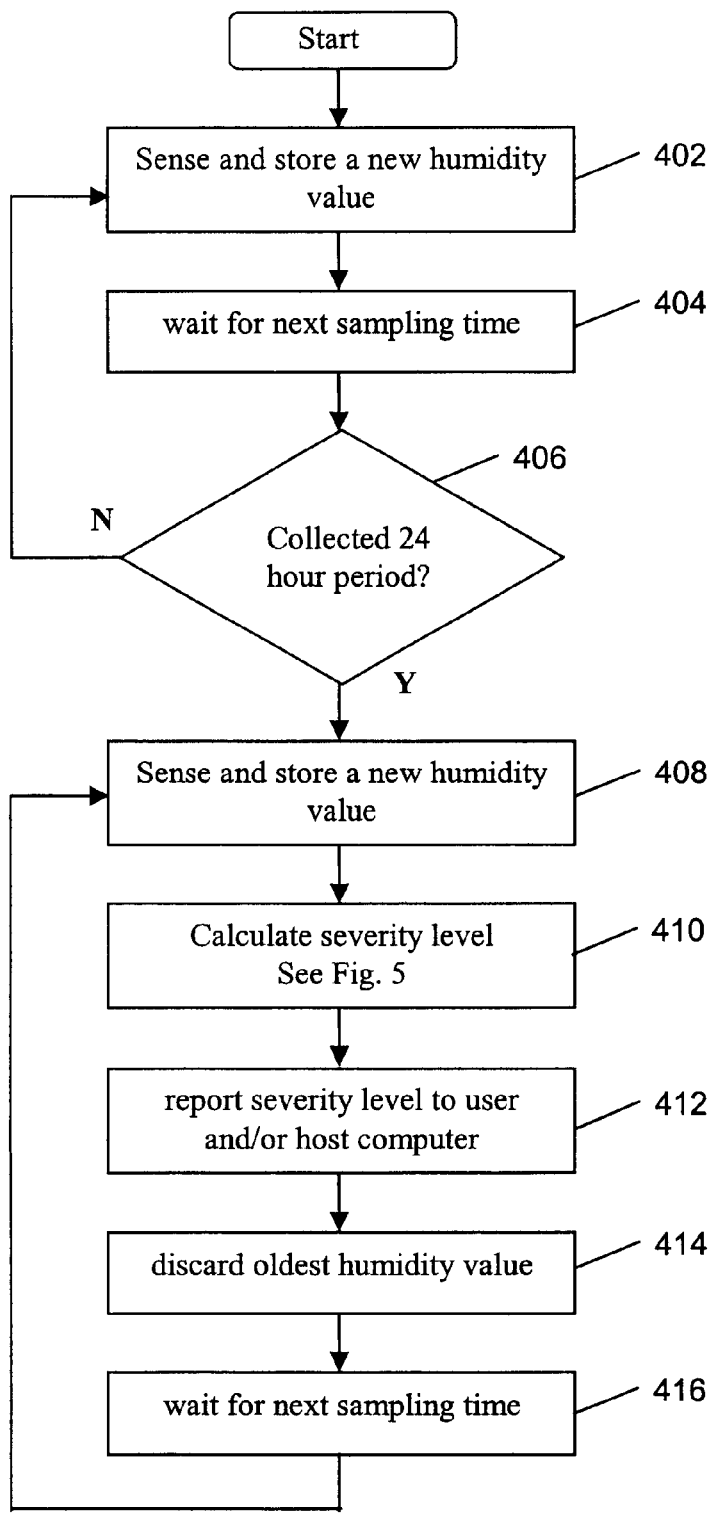
FIG. 4 is a flow diagram of the sampling algorithm.

An exemplary embodiment of a basic sampling algorithm is shown in FIG. 4. In the preferred embodiment, analysis begins after at least a 15-hour accumulation of samples has been collected and preferably after a full 24-hour day's accumulation of samples has been collected. The period over which the samples are accumulated is referred to herein as a predetermined data set scope. In the presently preferred embodiment, the control unit 202 collects a relative humidity sample from the relative humidity sensor 216 each hour. However, it is fully within the scope of the present invention to take samples more or less often if desired to gain a finer or coarser granularity. In order to achieve the full benefits of an algorithm disclosed herein, at least 8 samples are taken in a predetermined data set scope of 24 hours . Controller 202 desirably has enough storage space to contain evenly spaced samples over the predetermined data set scope. Once samples have been accumulated over the predetermined data set scope, the sampling algorithm will collect a new sample and call a severity algorithm to analyze the data at each new sampling interval. With this arrangement, a sliding window, extending for the previous 24 hours in the preferred embodiment, of data is available for analysis at each new sampling interval.

The sampling algorithm is defined in a manner known to those skilled in the art by executable instructions 209. This sampling algorithm begins in an initialization loop, by causing the control unit 202 to sense a relative humidity sample 402, from the relative humidity sensor 216. The controller 204 will then store this value in a table in the RAM 210, creating a historical data set of relative humidity samples. Next, the algorithm will wait for the next sampling time 404, one hour in the presently preferred embodiment. Then the algorithm tests to see if a fall-predetermined data set scope worth of samples has been collected 406. If not, the algorithm jumps back to sense a new relative humidity sample 402. If the full the predetermined data set scope worth of samples has been collected, the algorithm jumps down to the beginning of the operational loop 408.

The preferred embodiment described herein uses a 24-hour period and relative humidity samples at hourly intervals. The invention may use a longer or shorter period and any number of samples for creating the historical data set.

The operational loop begins by again sampling and storing a relative humidity value 408. After this latest relative humidity value is stored, the sampling algorithm calls the severity level algorithm 410. The severity level algorithm is described in detail below and shown in FIG. 5.

In this embodiment, the severity level algorithm will report a severity level between one and ten back to the sampling algorithm 410. Next, the control unit 202 reports 412 the severity level to the user through the notification panel 114, alarm LED 118, and audible alarm 112. Any notification value of five or greater is reported as a five. Additionally, if the growth condition meter 200 is attached to a host computer 300 through a network, the algorithm reports the full range of the severity level to the host computer 300.

After reporting, the oldest relative humidity value is discarded 414. This is may be thought of as a circular buffer containing enough sample points for the full predetermined data set scope (e.g., a 24-hour period). In this arrangement, incrementing the buffer pointer points to the next location in the circular buffer and when the next sample is written it will automatically overwrite the oldest value.

Then, the sampling algorithm waits 416 for the next sampling time. When this time is reached, the algorithm transitions back to the beginning of the operational loop 408.

Figure 5:
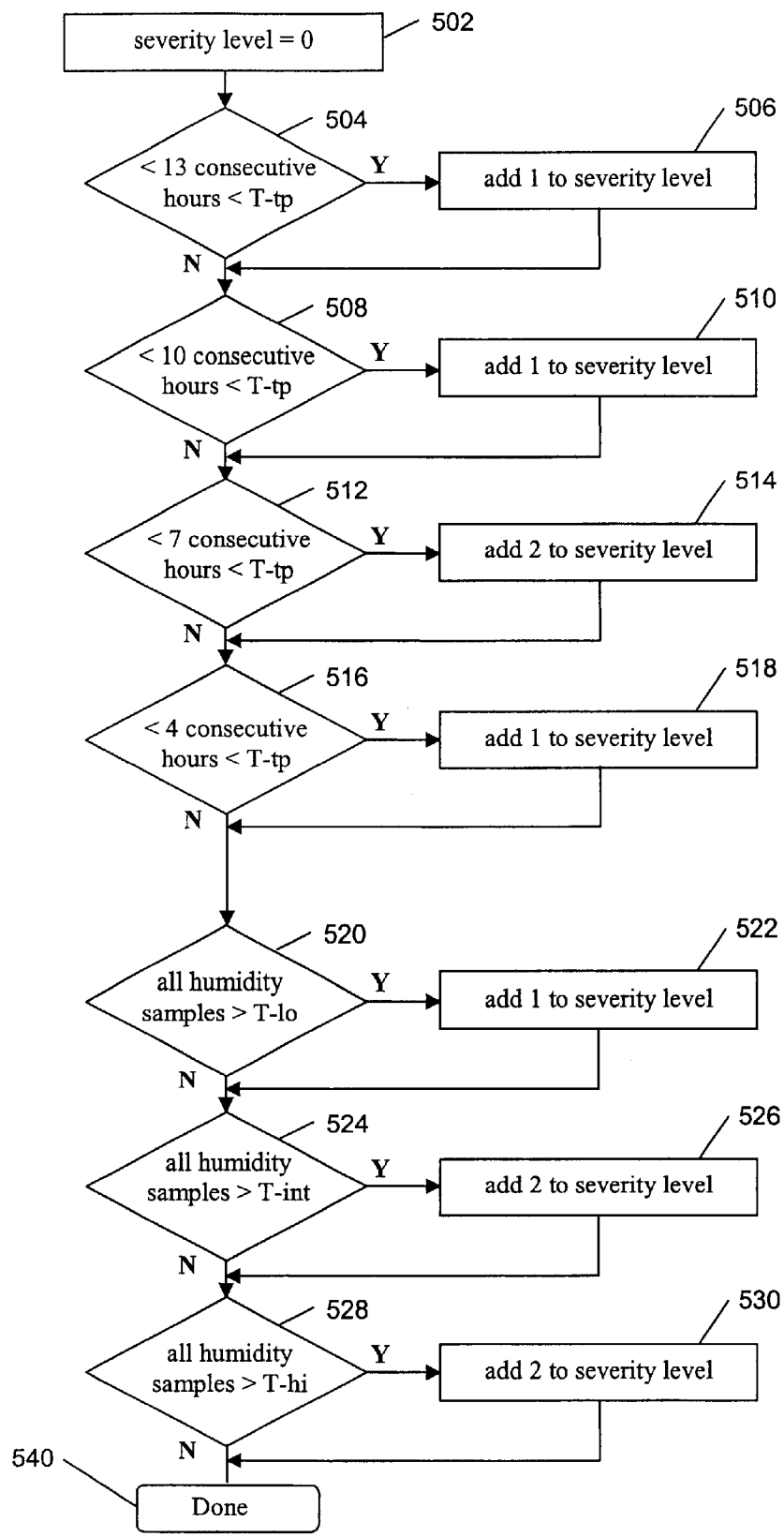
FIG. 5 is a flow diagram of the severity level determination algorithm.

An exemplary algorithm for determining the severity level is shown in FIG. 5. This algorithm is provided by executable instructions 209 in a manner well known to those skilled in the art. It represents a two-way analysis rubric for examining relative humidity in a cavity. For the preferred embodiment where the predetermined data set scope is a 24-hour period, the first rubric is a temporal analysis. This temporal analysis examines all consecutive samples over the previous 24-hour period to determine how much time was spent below a predetermined threshold. The second rubric is a baseline analysis comparing all samples over the previous 24-hour period to determine if all samples are over a predetermined baseline humidity threshold. The baseline rubric compensates for a scenario where there is enough time spent below the temporal threshold but the overall relative humidity remains high enough to promote fungal growth.

The analysis considers one temporal threshold and three different baseline humidity thresholds. The threshold levels are as follows:

T-tp—temporal humidity threshold;

T-hi—high baseline humidity threshold;

T-int—intermediate baseline humidity threshold; and

T-lo—low baseline humidity threshold.

These threshold levels are set to predetermined programmable values based on environmental conditions where the growth condition meter 200 will be installed. Example historical data collected in the Houston, Texas area indicate appropriate levels for the Houston area might be: T-tp=80%, T-hi=75%, T-int=70%, and T-lo=65%.

Figure 6:
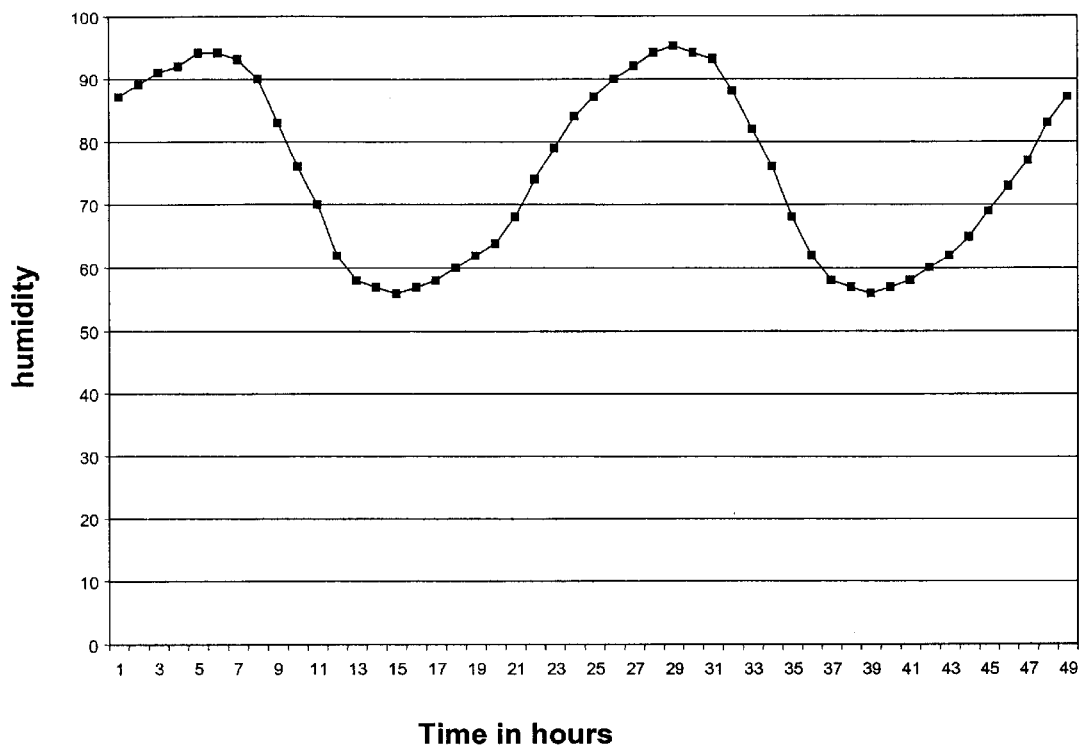
FIG. 6 is a graph of an example history of samples collected for a two-day period.

Relative humidity levels will typically by cyclical, following a roughly sinusoidal profile over a 24-hour period as shown in FIG. 6. Because of this, relative humidity may dip below T-tp twice during the 24-hour period, depending on what time of day marks the beginning of the 24-hour period being analyzed. Thus, if needed, the algorithm treats two discrete groupings of samples below T-tp as continuous for purpose of the analysis. As an example, using the data from FIG. 6, if the 24-hour period is measured from 12 to 36 and T-tp is set at 80%, there will be about 11 hours below 80%, then 10 hours above 80%, then 3 hours below 80%. These two separate periods below 80%, at the beginning and the end, are considered continuous for a total of 14 hours below T-tp. Another way to view this is to consider the first sample in the 24-hour period as adjacent to the last sample of the 24-hour period, in a circular buffer. In this way, the two areas below 80% are considered adjacent.

To begin the severity level algorithm, the severity level is set to zero 502. Next, the temporal analysis rubric is performed.

The temporal analysis rubric ensures that relative humidity changes in a cyclic fashion and that local relative humidity spends adequate time beneath the temporal humidity threshold. It begins by determining how much continuous time during the previous 24-hour period was spent below the temporal threshold. To determine continuous time spent below the temporal threshold, the algorithm examines sequential samples below T-tp. If less than thirteen consecutive hours are spent below T-tp 504, the algorithm increments the severity level 506. If not, the severity level is unchanged. Next, if less than ten consecutive hours are spent below T-tp 508, the severity level is incremented again 510, otherwise the severity level is not changed. Next, if less than seven hours are spent below T-tp 512, the severity level is incremented by two 514, otherwise the severity level is not changed. Next, if less than four hours are spent below T-tp 516, the severity level is incremented again 510, otherwise the severity level is not changed.

This completes the temporal analysis rubric creating a severity level based on how many consecutive hours are spent below the temporal humidity threshold T-tp. The severity level will be as follow:

13 to 10 hours below T-tp: severity level=1, 10 to 7 hours below T-tp: severity level=2, 7 to 4 hours below T-tp: severity level=4, less than 4 hours below T-tp: severity level=5.

The severity level jumps from two to four at around the seven-hour point because this is duration where the relative humidity variations are beginning to deviate from historical norms for the Houston area.

Of course, those skilled in the art will appreciate that an equivalent alternative analysis rubric could be based on the opposite polarities. For example, one may initiate the algorithms using a predetermined highly severe level, such as 10, then decrement from this value, with greater diminishment resulting from more time spent below the temporal threshold T-tp. In another alternative, one may achieve similar results by either increasing or decreasing severity level, as appropriate, based on the number of hours spent above the temporal threshold T-tp. These and other equivalent alternatives are included in the scope of the present invention.

Next, the baseline analysis may modify the severity level. In the baseline analysis rubric, all samples within the past 24-hour period are compared to the various baseline humidity threshold values. If all samples are above T-lo 520, the severity level is incremented by one 522, otherwise the severity level is not changed. Next, if all samples are above T-int 524, the severity level is incremented by two 526, otherwise the severity level is not changed. Next, if all samples are above T-hi 528, the severity level is incremented by two 530, otherwise the severity level is not changed.

This completes 540 the analysis for the current 24-hour period creating an additional amount added to the severity level based on the baseline analysis as follows:

all samples above t-lo severity level incremented by an additional 1, all samples above t-int severity level incremented by an additional 3, all samples above t-hi severity level incremented by an additional 5.

From the combination of both rubrics, a severity level of zero to ten is possible.

Specific embodiments have been shown by way of example in the drawings and have been described in detail herein, however the invention may be susceptible to various modifications and alternative forms. For example, the baseline analysis, like the temporal analysis, may be modified into a variety of equivalent algorithms. Such algorithms may increment or decrement severity level, as appropriate, based on all or most samples being either above or below appropriate thresholds. It should be understood that the invention is not intended to be limited to the particular forms disclosed. Rather, the invention includes all modifications, equivalents, and alternatives falling within the spirit and scope of the invention as defined by the following appended claims.

What is claimed is:

1. A method of detecting environmental conditions conducive to mold growth within a cavity of a building comprising:

sensing a relative humidity value;

repeating the sensing of a relative humidity value from time to time;

creating a historical data set by storing the relative humidity values from at least two sequential iterations of the sensing activity;

analyzing the historical data set to determine a severity level based upon when at least one predetermined humidity threshold is exceeded; and notifying a user of the severity level.

2. The method of claim 1, wherein analyzing the historical data set comprises increasing the severity level when the historical data set indicates that the relative humidity has remained greater than a first baseline humidity for a predetermined data set scope, said predetermined data set scope being greater than 15 hours.

3. The method of claim 1, wherein analyzing the historical data set comprises increasing the severity level when relative humidity values in the historical data set indicate relative humidity below the temporal humidity threshold for a period of time less than a first duration.

4. The method of claim 1, wherein analyzing the historical data set comprises:

increasing the severity level when the historical data set indicates that the relative humidity has remained greater than a first baseline humidity for a predetermined data set scope, said predetermined data set scope being greater than 15 hours; and increasing the severity level when relative humidity values in the historical data set indicate relative humidity below the temporal humidity threshold for a period of time less than a first duration.

5. The method of claim 4, wherein analyzing the historical data set further comprises:

additionally increasing the severity level when relative humidity values in the historical data set indicate relative humidity below the temporal humidity threshold for a period of time less than a second duration, the second duration being less than the first duration;

additionally increasing the severity level when relative humidity values in the historical data set indicate relative humidity below the temporal humidity threshold for a period of time less than a third duration, the third duration being less than the second duration;

additionally increasing the severity level when relative humidity values in the historical data set indicate relative humidity below the temporal humidity threshold for a period of time less than a fourth duration, the fourth duration being less than the third duration.

6. The method of claim 5 wherein:

the temporal humidity threshold is about 80%;

the first duration is about 13 hours;

the second duration is about 10 hours;

the third duration is about 7 hours; and the fourth duration is about 4 hours.

7. The method of claim 4, wherein analyzing the historical data set further comprises:

additionally increasing the severity level when the historical data set indicates that the relative humidity has remained greater than a second baseline humidity for the predetermined data set scope, the second baseline humidity threshold being greater than the first baseline humidity threshold; and additionally increasing the severity level when the historical data set indicates that the relative humidity has remained greater than a third baseline humidity for the predetermined data set scope, the third baseline humidity threshold being greater than the second baseline humidity threshold.

8. The method of claim 7, wherein:

the first baseline humidity threshold is about 65%;

the second baseline humidity threshold is about 70%; and the third baseline humidity threshold is about 75%.

9. The method of claim 1, wherein the step of notifying a user further comprises transmitting the severity level to a host computer.

10. The method of claim 1, wherein the historical data set includes at least eight relative humidity values from iterations of the sensing activity performed over the previous 24 hours.

11. The method of claim 10 wherein the historical data set includes at least 24 relative humidity values from iterations of the sensing activity performed over the previous 24 hours.

12. A system for detecting environmental conditions conducive to mold growth within a cavity of a building comprising:

a controller;

a relative humidity sensor operably coupled to the controller;

a memory operably coupled to the controller, wherein a set of relative humidity values sensed by the relative humidity sensor during a set of sampling events are stored in the memory;

a set of executable instructions are stored in the memory for execution by the controller, the set of executable instructions being configured to control the relative humidity sensor and execute a humidity analysis algorithm for determining environmental conditions conducive to mold growth by analyzing the set of relative humidity values relative to at least one predetermined humidity threshold; and a user interface operably coupled to the controller for reporting results of the humidity analysis algorithm as a severity level.

13. The system of claim 12, further comprising a network interface.

14. The system of claim 12, wherein the user interface comprises a user notification panel for indicating the severity level.

15. The system of claim 14, wherein the user interface further comprises a visual alarm indicating a severity level wherein a growth condition deviating from historical norms has been reached.

16. The system of claim 14, wherein the user interface further comprises an audio alarm indicating a severity level wherein a growth condition deviating from historical norms has been reached.

17. A system for detecting environmental conditions conducive to mold growth within a cavity of a building comprising:

a host computer; and at least one growth condition meter within at least one cavity of a building operably coupled to the host computer, comprising:

a controller;

a relative humidity sensor operably coupled to the controller;

a memory operably coupled to the controller, wherein a set of relative humidity values sensed by the relative humidity sensor during a set of sampling events are stored in the memory, and a set of executable instructions are stored in the memory for execution by the controller, the set of executable instructions being configured to control the relative humidity sensor and execute a humidity analysis algorithm for determining environmental conditions conducive to mold growth by analyzing the set of relative humidity values relative to at least one predetermined humidity threshold; and a user interface for reporting results of the humidity analysis algorithm as a severity level.

18. The system of claim 17, wherein the user interface comprises a user notification panel for indicating the severity level.

19. The system of claim 17, wherein the user interface further comprises a visual alarm indicating a severity level wherein a growth condition deviating from historical norms has been reached.

20. The system of claim 15, wherein the user interface further comprises, an audio alarm indicating a severity level wherein a growth condition deviating from historical norms has been reached.

* * * * *

UNITED STATES PATENT AND TRADEMARK OFFICE
CERTIFICATE OF CORRECTION

PATENT NO. : 6,704,681 B1
DATED : March 9, 2004
INVENTOR(S) : Russell S. Nassof et al.

It is certified that error appears in the above-identified patent and that said Letters Patent is hereby corrected as shown below:

<u>Title page,</u>
Item [73], Assignee, delete "Envirnomics" and replace with -- Environomics --.

Signed and Sealed this

Twenty-second Day of June, 2004

JON W. DUDAS
*Acting Director of the United States Patent and Trademark Office*